United States Patent
Dorenkamp et al.

(10) Patent No.: US 7,287,388 B2
(45) Date of Patent: Oct. 30, 2007

(54) CRYOSTAT HAVING AN INTEGRATED STAINING STATION

(75) Inventors: Claudia Dorenkamp, Muehlhausen (DE); Stefan Kuenkel, Karlsruhe (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 327 days.

(21) Appl. No.: 10/991,274

(22) Filed: Nov. 17, 2004

(65) Prior Publication Data

US 2005/0109045 A1    May 26, 2005

(30) Foreign Application Priority Data

Nov. 22, 2003   (DE) ................................ 203 18 093

(51) Int. Cl.
- *F25B 19/00* (2006.01)
- *F25B 25/00* (2006.01)
- *B32B 5/02* (2006.01)
- *B32B 27/04* (2006.01)
- *B01L 3/00* (2006.01)

(52) U.S. Cl. ............................ 62/51.1; 62/322; 422/65; 422/99

(58) Field of Classification Search ................. 62/51.1, 62/322; 422/65, 99
See application file for complete search history.

(56) References Cited

U.S. PATENT DOCUMENTS

| | | | |
|---|---|---|---|
| 3,456,538 A * | 7/1969 | Barton et al. ................. 83/171 |
| 4,548,051 A * | 10/1985 | Moessner ..................... 62/320 |
| 4,979,376 A * | 12/1990 | Biehl et al. .................... 62/264 |
| 5,156,019 A * | 10/1992 | McCormick .................. 62/320 |
| 5,533,342 A * | 7/1996 | Gordon ........................ 62/51.1 |
| 5,601,650 A * | 2/1997 | Goldbecker et al. ......... 118/697 |
| 6,372,512 B1 * | 4/2002 | Kerschmann ................ 436/174 |
| 6,387,653 B1 * | 5/2002 | Voneiff et al. ........... 435/40.52 |
| 6,635,225 B1 | 10/2003 | Thiem et al. |
| 2002/0139124 A1 * | 10/2002 | Palermo ...................... 62/51.1 |
| 2003/0059764 A1 * | 3/2003 | Ravkin et al. .................. 435/4 |

* cited by examiner

Primary Examiner—William C Doerrler
(74) Attorney, Agent, or Firm—Hodgson Russ LLP

(57) ABSTRACT

A cryostat (1) having a sealable housing (2) is described. The housing (2) encloses a coolable cryostat chamber (3), and a refrigeration device (4), a control system (5) and a power supply (6) are provided for cooling the cryostat chamber (3). For cutting frozen samples, a microtome is arranged in the cryostat chamber (3), a staining station (7) being integrated into the housing (2) outside the cryostat chamber (3).

8 Claims, 1 Drawing Sheet

CRYOSTAT HAVING AN INTEGRATED STAINING STATION

CROSS REFERENCE TO RELATED APPLICATIONS

This application claims priority of the German utility model application 203 18 093.3 filed Nov. 22, 2003, which is incorporated by reference herein.

FIELD OF THE INVENTION

The invention concerns a cryostat having a cryostat chamber in which a microtome for cutting frozen specimens is arranged.

BACKGROUND OF THE INVENTION

Such cryostats are used in order to cut frozen specimens with a microtome for subsequent viewing with a microscope. The preparations to be cut are cooled to a specific predefined temperature, the temperatures in this context generally being between −10° C. and −50° C. In order to achieve these temperatures, an appropriately dimensioned refrigeration device, with which a control system and a central power supply are associated, is provided in the cryostat.

To ensure a constant temperature, the microtomes are arranged in complexly encapsulated cryostat chambers, and the latter are correspondingly cooled with the refrigeration device.

The frozen specimens are cut using a microtome arranged in the cryostat chamber, and then transferred from the knife or knife holder onto a specimen slide and stained. A variety of staining methods can be used depending on the specimen being cut; the specimens on the specimen slides must pass in succession through different containers.

A stainer having several containers arranged one behind another is known from DE 199 18 442 A1. This stainer has proven very successful in practical use, and is optimized for a high throughput of slides. Because of its physical size, the stainer is set up at a separate workstation in the laboratory, and therefore not directly accessible next to the cryostat.

In practical use, the frozen and cut specimens need to be microscopically examined as quickly as possible. In order to ensure the requisite staining of the cut specimens as quickly as possible, simple staining containers are placed on the cryostat and staining is performed there. Since the containers are not directly joined to the cryostat, the danger exists that the containers will tip over and the contents will spill into the cryostat chamber. As a result, it is no longer possible to work with the cryostat, because a defrosting and laborious cleaning operation must first be performed.

SUMMARY OF THE INVENTION

It is therefore the object of the present invention to improve the operating reliability of the cryostat, to ensure ergonomic operation, and to automate manual staining.

This object is achieved by a cryostat according to the invention characterized in that a staining station is permanently integrated into the housing of the cryostat and outside the cryostat chamber, so there is no danger that staining containers will tip over.

In an embodiment of the invention, the staining station comprises several staining containers arranged next to one another, so that several specimens can be stained simultaneously or can pass through the staining process with several fluids in succession.

In a refinement of the invention, the staining station is equipped with a transport apparatus and a drive motor for transporting specimen slides into adjacent staining containers so that the specimen slides having the specimens to be stained are transported automatically.

In a further embodiment of the invention, the staining station is electrically connected to the control system and/or to the power supply, so that a separate control system and/or power supply is not necessary. The necessary control functions can be performed directly via the cryostat control system.

In a further embodiment of the invention, the drive motor is electrically connected to the control system and/or to the power supply, so that a separate control system and/or power supply is not necessary. The necessary control functions can be performed directly via the cryostat control system.

In a further embodiment of the invention, the transport apparatus is equipped with a chain drive with which the specimen slides are transported from one container into the next.

In a further embodiment of the invention, a setting unit for adjusting modifiable parameters of the staining station, such as staining time, drain time, and temperature, is associated with the control system. The setting unit is thus directly integrated into the housing of the cryostat, and the setting unit of the cryostat can also handle the input functions for the staining station.

In a refinement of the invention, the staining station is arranged in the housing of the cryostat at lectern height (approx. 110 cm), thus also making possible ergonomic operation when specimen slides are put into and removed from the staining station.

BRIEF DESCRIPTION OF THE DRAWINGS

The invention will be explained in more detail with reference to FIG. 1, which shows, in schematic fashion, a cryostat formed in accordance with an exemplary embodiment of the present invention.

DETAILED DESCRIPTION OF THE INVENTION

Figure 1:
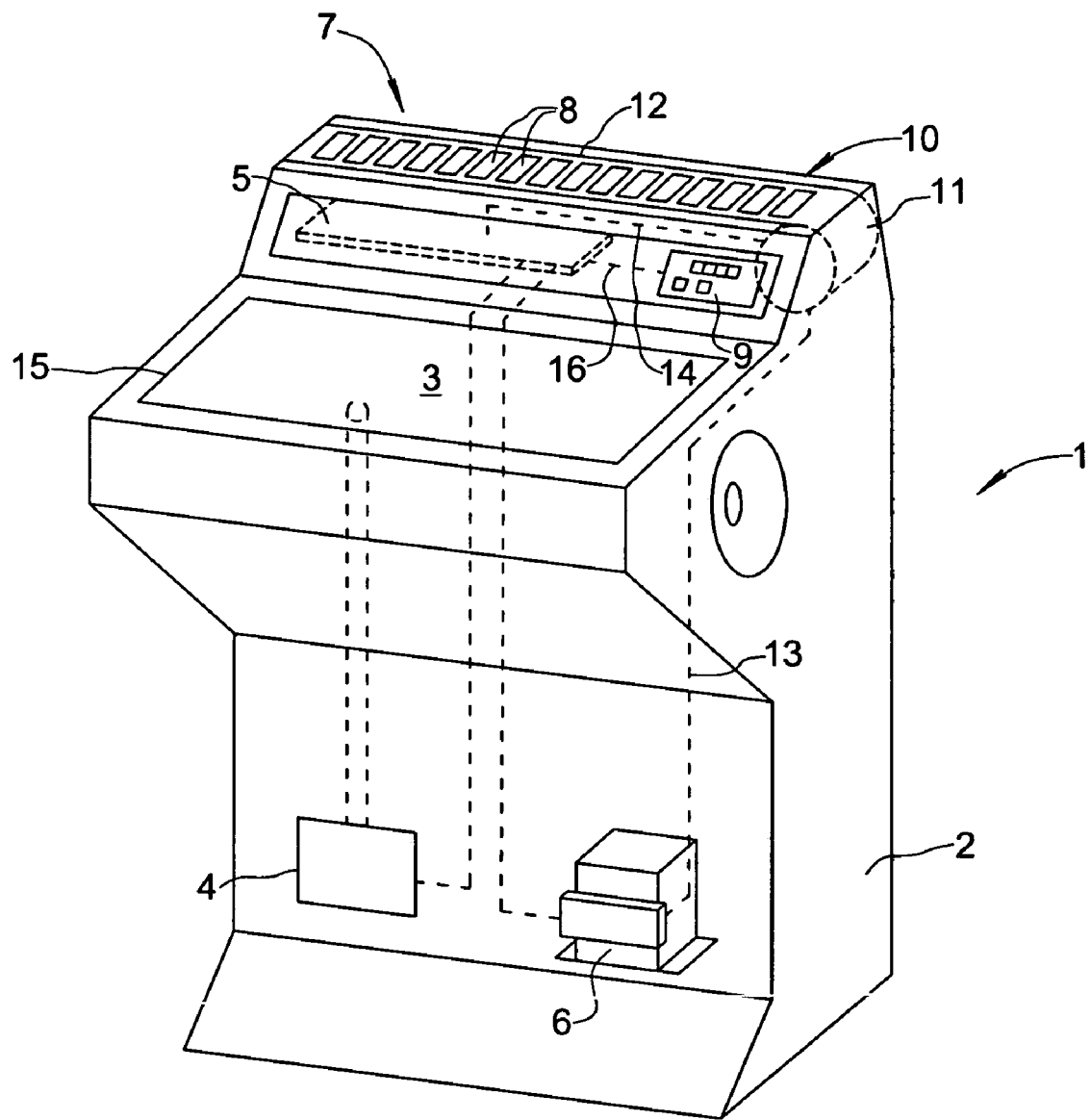

FIG. 1 is a view of a cryostat 1 having a housing 2 that encloses a cryostat chamber 3 in which a microtome (not depicted) is arranged. Cryostat chamber 3 is accessible to the user via a cover 15. A refrigeration device 4 is arranged in housing 2 in order to cool cryostat chamber 3. A control system 5 and a central power supply 6 are provided for the operation of cryostat 1. A staining station 7, for staining cut specimens arranged on specimen slides, is integrated into housing 2 of cryostat 1. Staining station 7 comprises several staining containers 8 arranged next to one another, and is equipped with a transport apparatus 10. Transport apparatus 10 comprises a chain drive 12 as well as a drive motor 11 that is connected via a first electrical connection 13 to central power supply 6.

Staining station 7 is connected via a second electrical connection 14 to control system 5. A setting unit 9, which is connected via an electrical connection 16 to control system 5, is provided for manual definition of specific cycle times and/or temperatures in staining station 7.

Staining station 7 is dimensioned in such a way that several specimen slides can be stained simultaneously, staining station 7 being arranged in housing 2 of cryostat 1 at normal lectern height, i.e. approx. 110 cm. It is thus possible to work in ergonomically favorable fashion when staining the specimens on the specimen slides.

PARTS LIST

1 Cryostat
2 Housing
3 Cryostat chamber
4 Refrigeration device
5 Control system
6 Power supply
7 Staining station
8 Staining container
9 Setting unit
10 Transport apparatus
11 Drive motor
12 Chain drive
13 Electrical connection 6-11
14 Electrical connection 5-11
15 Cover
16 Electrical connection 5-9

What is claimed is:

1. A cryostat for containing a microtome in a temperature-controlled environment, the cryostat comprising:
   a housing enclosing a cryostat chamber;
   a refrigeration device communicating with the cryostat chamber for cooling the cryostat chamber;
   a control system electrically connected to the refrigeration device;
   a power supply electrically connected to the control system; and
   a staining station integrated into the housing outside the cryostat chamber,
   wherein the staining station includes a plurality of staining containers, the staining station further includes a motor-driven transport apparatus for transporting specimen slides from one staining container to another staining container, the staining station is electrically connected to the control system, the motor-driven transport apparatus has a drive motor electrically connected to the power supply, and the staining station is integrated into the housing of the cryostat at lectern height or at substantially lectern height.

2. The cryostat as defined in claim 1, wherein the staining station is electrically connected to the power supply.

3. The cryostat as defined in claim 1, wherein the motor-driven transport apparatus has a drive motor electrically connected to the control system.

4. The cryostat as defined in claim 1, wherein the transport apparatus has a chain drive.

5. A cryostat for containing a microtome in a temperature-controlled environment, the cryostat comprising:
   a housing enclosing a cryostat chamber;
   a refrigeration device communicating with the cryostat chamber for cooling the cryostat chamber;
   a control system electrically connected to the refrigeration device;
   a power supply electrically connected to the control system;
   a staining station integrated into the housing outside the cryostat chamber; and, a setting unit electrically connected to the control system for adjusting modifiable parameters of the staining station.

6. The cryostat as defined in claim 5, wherein the modifiable parameters include at least one parameter chosen from a group of modifiable parameters consisting of staining time, drain time, and temperature.

7. A cryostat as defined in claim 1, wherein the transport apparatus is confined to the staining station.

8. A cryostat as defined in claim 5, further comprising a motor-driven transport apparatus for transporting specimen slides from one staining container to another staining container, wherein the transport apparatus is confined to the staining station.

* * * * *